US 8,823,787 B2

(12) United States Patent
Kibayashi

(10) Patent No.: US 8,823,787 B2
(45) Date of Patent: Sep. 2, 2014

(54) IMAGE PICKUP APPARATUS

(71) Applicant: Olympus Medical Systems Corp., Tokyo (JP)

(72) Inventor: Takehide Kibayashi, Yamato (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/646,058

(22) Filed: Oct. 5, 2012

(65) Prior Publication Data
US 2013/0027534 A1   Jan. 31, 2013

Related U.S. Application Data

(63) Continuation of application No. PCT/JP2012/058970, filed on Apr. 2, 2012.

(30) Foreign Application Priority Data

Apr. 5, 2011   (JP) ................. 2011-083849

(51) Int. Cl.
*A62B 1/04* (2006.01)
*H04N 7/18* (2006.01)
*H04N 9/47* (2006.01)
*G02B 15/14* (2006.01)
*G02B 23/24* (2006.01)
*A61B 1/00* (2006.01)
*G02B 7/10* (2006.01)
*A61B 1/05* (2006.01)

(52) U.S. Cl.
CPC .............. *G02B 7/10* (2013.01); *G02B 23/2438* (2013.01); *A61B 1/00096* (2013.01); *A61B 1/05* (2013.01)
USPC ............................................ 348/65; 359/694

(58) Field of Classification Search
CPC ........ A61B 1/00096; A61B 1/05; G02B 7/10; G02B 23/2438
USPC ................................................................ 348/65
See application file for complete search history.

(56) References Cited

U.S. PATENT DOCUMENTS

| | | | |
|---|---|---|---|
| 5,661,609 A * | 8/1997 | Asakura et al. | 359/826 |
| 5,933,285 A * | 8/1999 | Sato et al. | 359/694 |
| 6,507,700 B1 | 1/2003 | Takekuma et al. | |

FOREIGN PATENT DOCUMENTS

| | | |
|---|---|---|
| JP | 08-240760 A | 9/1996 |
| JP | 2002-090603 A | 3/2002 |
| JP | 2005-334509 A | 12/2005 |
| JP | 2008-118568 A | 5/2008 |
| JP | 2008-307293 A | 12/2008 |

* cited by examiner

*Primary Examiner* — Hee-Yong Kim
(74) *Attorney, Agent, or Firm* — Scully, Scott, Murphy & Presser, P.C.

(57) ABSTRACT

A second lens frame has a shape including: a contact portion having a cylindrical shape with a diameter smaller than an inner diameter of a space portion of a first lens frame, a distal end portion thereof being brought into contact with an end face of the first lens frame; and a fitting portion having a diameter larger than that of the contact portion in a cylindrical shape fitting on an inner wall surface of the first lens frame, and when the second lens frame is inserted into the space portion of the first lens frame, a gap is formed therebetween. Accordingly, a distal end portion of the second lens frame is reliably brought into contact with an end face of a flange portion of the first lens frame, whereby variations in position in an optical axis direction are eliminated, enabling provision of a stable optical precision.

2 Claims, 4 Drawing Sheets

IMAGE PICKUP APPARATUS

CROSS REFERENCE TO RELATED APPLICATION

This application is a continuation application of PCT/JP2012/058970 filed on Apr. 2, 2012 and claims benefit of Japanese Application No. 2011-083849 filed in Japan on Apr. 5, 2011, the entire contents of which are incorporated herein by this reference.

BACKGROUND OF THE INVENTION

1. Field of the Invention

The present invention relates to an image pickup apparatus including an image pickup system disposed at a rear of an objective optical system.

2. Description of the Related Art

In recent years, industrial and medical endoscopes have been widely used. In particular, there are endoscopes including an image pickup apparatus using a solid image pickup device such as a CCD arranged at a distal end of an insertion portion thereof. The insertion portion in which the image pickup apparatus is arranged is inserted into, for example, a body cavity in the case of a medical endoscope, enabling an image of a site to be examined in the body cavity to be observed via a monitor.

As disclosed in Japanese Patent Application Laid-Open Publication No. 2008-307293, in order to achieve downsizing and enhancement in assemblability, in an image pickup apparatus incorporated in a distal end portion of such endoscope, an image pickup device package is disposed at a rear of an objective optical system including a group of lenses. The image pickup device package is formed by packaging a solid image pickup device, a cover glass that protects an image pickup surface of the solid image pickup device and a circuit substrate with electronic components mounted thereon on a rear face opposite to the image pickup surface of the solid image pickup device by means of sealing using a resin.

In general, a group of lenses included in an objective optical system in an image pickup apparatus are held using a lens frame. In such lens frame-used lens holding structure, the group of lenses may be held by a plurality of lens frames, and in such case, in order to accurately hold optical positions of the respective lenses to ensure optical performance, a lens holding structure such as illustrated in FIG. 5 is often provided to dispose an image pickup device package at the rear of the lens holding structure.

In the lens holding structure illustrated in FIG. 5, a first lens frame 210 holding one lens 200 included in an objective lens group is joined to a second lens frame 211 holding the other lens 201 by making the second lens frame 211 butt an inner portion of the first lens frame 210, whereby the lenses 200 and 201 are disposed at prescribed positions in an optical axis direction, and an image pickup frame 212 holding a non-illustrated image pickup device package is joined to the second lens frame 211.

SUMMARY OF THE INVENTION

An image pickup apparatus according to an aspect of the present invention provides an image pickup apparatus including an image pickup system disposed at a rear of an objective optical system, wherein the objective optical system includes a plurality of lenses and a plurality of lens frames, and in at least two lens frames of the plurality of lens frames, a first lens frame includes a step portion inside, which a distal end portion of a second lens frame is brought into contact with, the second lens frame includes a fitting portion that fits in an inner diameter of the first lens frame, and a contact portion that provides a gap between the inner diameter of the first lens frame and the contact portion, the contact portion being brought into contact with the step portion.

An image pickup apparatus according to another aspect of the present invention provides an image pickup apparatus including an image pickup system disposed at a rear of an objective optical system, wherein the objective optical system includes a plurality of lenses and a plurality of lens frames, and in a configuration of at least two lens frames of the plurality of lens frames, a first lens frame includes a step portion and a slide portion inside, the step portion allowing a distal end portion of a second lens frame to be brought into contact therewith and the slide portion having a moving lens frame disposed thereon, which advances and retracts in an optical axis direction, on a front side of the step portion, the second lens frame includes a fitting portion that fits in an inner diameter of the first lens frame and a contact portion that provides a gap between the inner diameter of the first lens frame and the contact portion and is brought into contact with the step portion.

An image pickup apparatus according to still another aspect of the present invention provides an image pickup apparatus including an image pickup system disposed at a rear of an objective optical system that includes a plurality of lenses aligned in an optical axis direction, the image pickup apparatus comprising: a first lens frame that holds a part of the plurality of lenses; a second lens frame that holds a part of the plurality of lenses, and moves along an optical axis direction and fits on an inner circumferential face of the first lens frame; a fitting portion provided at an outer circumference of the second lens frame, the fitting portion fitting on the inner circumferential face of the first lens frame; a small-diameter portion provided on the movement direction side relative to the fitting portion at the outer circumference of the second lens frame, the small-diameter portion having an outer diameter smaller than an outer diameter of the fitting portion, thereby forming a gap between the small-diameter portion and the inner circumferential face of the first lens frame; and a contact surface that is provided at an inner circumference of the first lens frame, and when the second lens frame is fitted in the first lens frame, allows a distal end face of the small-diameter portion of the second lens frame to come into contact with the contact surface.

DETAILED DESCRIPTION OF THE PREFERRED EMBODIMENTS

Figure 1:
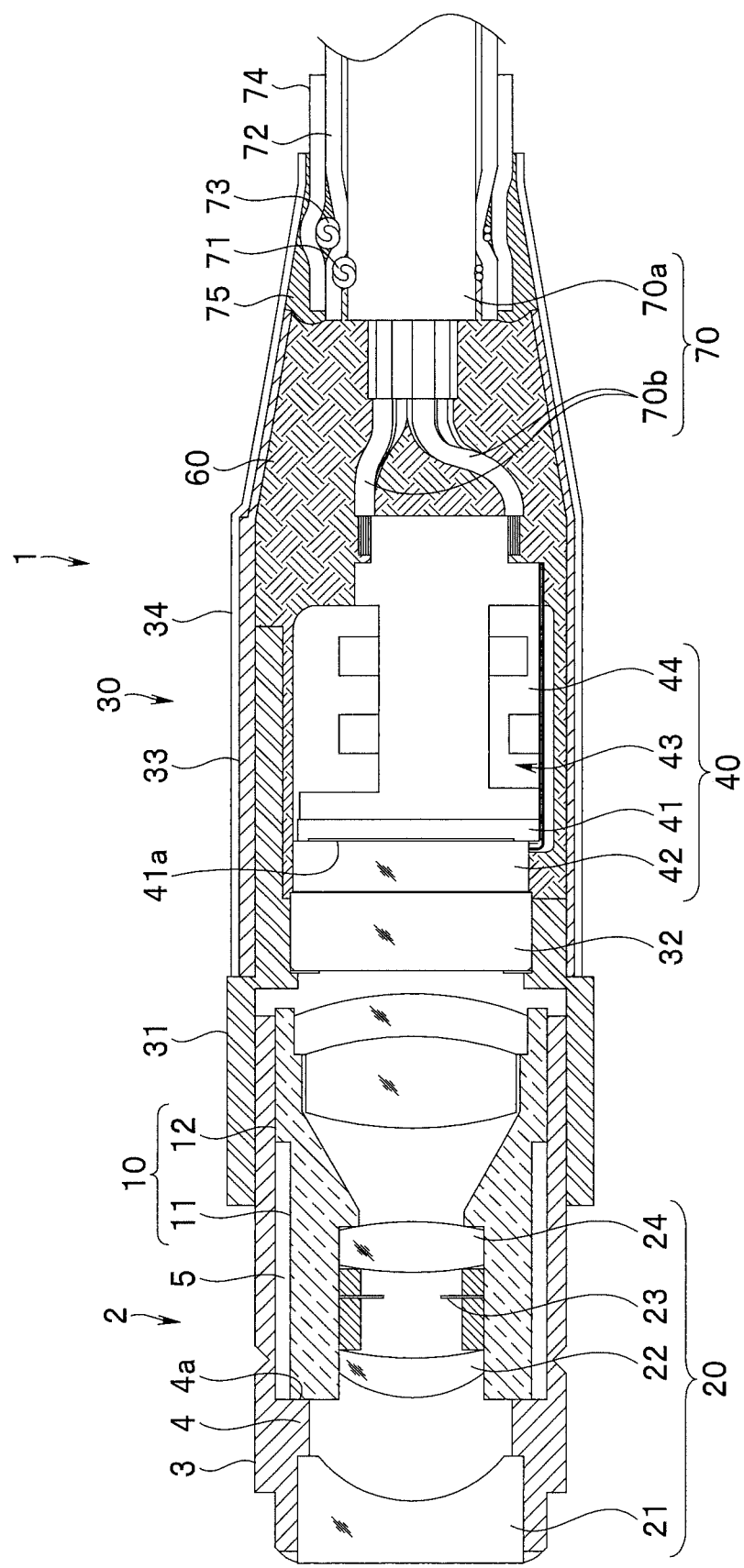
FIG. 1 relates to a first embodiment of the present invention and is a configuration diagram illustrating an image pickup apparatus provided at a distal end of an insertion portion of an endoscope.

A first embodiment of the present invention will be described below with reference to FIGS. 1 to 3.

An image pickup apparatus according to the present invention is one employed in, for example, an endoscope including an image pickup device incorporated on the distal end side of an elongated insertion portion, which is inserted into a cavity in a site to be observed. As illustrated in FIG. 1, such image pickup apparatus 1 includes an objective optical system unit 2, and an image pickup system unit 30 arranged at the rear of the objective optical system unit 2.

The objective optical system unit 2 holds an objective lens group 20, which includes a plurality of lenses, via a first lens frame 3 and a second lens frame 10 joined to the first lens frame 3. In the present embodiment, from among the objective lens group 20, a first lens 21 on the distal end side is held by the first lens frame 3 and a group of remaining lenses is held by the second lens frame 10. Furthermore, the respective lenses in the objective lens group 20 are disposed at sites of the respective lens frames where perpendicularity and coaxiality are provided by means of high-precision processing. With such structure, the respective lenses in the objective lens group 20 are disposed in the respective lens frames without inclination.

The first lens frame 3 is formed in a substantially-cylindrical shape, and at a position close to a distal end in an inner portion of the cylindrical shape, a flange portion 4 that allows an outer circumferential portion on the proximal end side of the first lens 21 to be brought into contact therewith is provided. On the rear side of the flange portion 4, a space portion in which a second lens frame 10 is received is provided. Note that if the first lens frame 3 is employed in, for example, an endoscope, the first lens frame 3 is fitted in a distal end frame of the endoscope, which is not illustrated, and held by a distal end portion of the endoscope. Furthermore, the outer circumferential portion of the first lens 21 held by the first lens frame 3 is joined in an air-tight manner to the first lens frame 3 by means of soldering or brazing, for example, taking autoclave sterilization processing into account.

Furthermore, the second lens frame 10 holds the group of remaining lenses other than the first lens 21 in the objective lens group 20, and thus holds a second lens 22, a diaphragm 23, a third lens 24, a fourth lens 25 and a fifth lens 26 disposed at the rear of the first lens 21 in this order from the distal end side. The second lens frame 10 holding such group of lenses is inserted into the space portion provided on the rear side of the flange portion 4 of the first lens frame 3, and a distal end portion of the second lens frame 10 is brought into contact with an end face 4a on the rear side of the flange portion 4 of the first lens frame 3, and a rear end portion of the second lens frame 10 is fitted on an inner wall surface of the space portion of the first lens frame 3 and fixed via, e.g., an adhesive.

More specifically, an outer shape of the second lens frame 10 is formed to be a stepped cylindrical shape in which the distal end side and the rear end side have different outer diameters, and the second lens frame 10 includes a contact portion 11 having a cylindrical shape with a diameter smaller than that of an inner diameter of the space portion of the first lens frame 3, a distal end portion of the contact portion 11 being brought into contact with the end face 4a on the rear side of the flange portion 4 of the first lens frame 3, and a cylindrically-shaped fitting portion 12 provided over a predetermined length on the rear end side of the contact portion 11, the fitting portion 12 having a diameter larger than that of the contact portion 11 and being fitted on the inner wall surface of the space portion of the first lens frame 3. In other words, the second lens frame 10 is formed so as to have a shape that forms a gap 5 between the inner wall surface of the space portion of the first lens frame 3 and the second lens frame 10 when the second lens frame 10 is inserted into the space portion of the first lens frame 3. Also, a surface of the distal end portion of the second lens frame 10 and the end face 4a of the flange portion 4 of the first lens frame 3 are processed so as to have highly-precise perpendicularity to the optical axis. Furthermore, the fitting portion 12 is processed so as to have highly-precise coaxiality relative to the optical axis.

As a result of provision of such gap 5, when the second lens frame 10 is inserted and fitted in the first lens frame 3, the area of contact between the first lens frame 3 and the second lens frame 10 is reduced and the insertion resistance is thereby reduced, enabling enhancement in assembling workability. In addition, the distal end portion of the second lens frame 10 can reliably be brought into contact with the end face 4a of the flange portion 4 of the first lens frame 3, whereby variations in coaxiality and/or perpendicularity and/or position in the optical axis direction between the first lens 21 disposed in the first lens frame 3 and the group of remaining lenses disposed inside the second lens frame 10 are eliminated, enabling prevention of optical performance deterioration.

Also, in order to provide optical precision, it is only necessary that only the rear end portion is fitted, and thus, the length of the fitting portion that requires a precise dimensional tolerance can be reduced, and if there is difficulty in processing the frame, employment of the present structure provides a cost reduction effect. Furthermore, when the second lens frame 10 is fitted into the first lens frame 3, no undue load is imposed on the lens-attached portions, and thus, optical position deviations due to displacement of the lens-attached portions can be prevented, ensuring that worst situations such as lens breakage is avoided.

Furthermore, when an adhesive is applied to the fitting portion 12 of the second lens frame 10 and the fitting portion 12 is assembled into the first lens frame 3, even if the adhesive applied on the fitting portion 12 flows toward the distal end side, the adhesive can be confined inside the gap 5, and does not flow between the end face 4a of the flange portion 4 of the first lens frame 3 and a distal end of the contact portion 11 of the second lens frame 10. Accordingly, no misalignment in the optical axis direction among the lenses by the amount of a thickness of the layer of the flowed-in adhesive resulting from the adhesive flowing to the contact surface occurs, ensuring provision of a stable optical precision.

The above-described objective optical system unit 2 is joined to the image pickup system unit 30, and incoming light entering via the objective lens group 20 forms an image on a light-receiving surface of a solid image pickup device 41 inside the image pickup system unit 30. Then, the optical image of a subject/object is subjected to photoelectric conversion by the solid image pickup device 41, and an image pickup signal resulting from the photoelectric conversion is transmitted to a following signal processing circuit via a signal cable 70.

The objective optical system unit 2 and the image pickup system unit 30 are joined to each other by inserting and fitting the first lens frame 3 with the second lens frame 10 received and fixed thereto into an inner diameter portion of an image pickup frame 31 holding the image pickup device package 40 and joining these two members to each other in an air-tight manner. The image pickup device package 40 is one resulting from unitization by means of integral molding using an insulating sealing resin 44. The integral molding is performed after a cover glass 42 for protection is fixed to an image pickup surface 41a of the solid image pickup device 41 that includes, e.g., a CMOS or a CCD by means of adhesion using, e.g., an ultraviolet cure adhesive, a circuit substrate portion 43 with a plurality of electronic components such as capacitors, resistances and/or transistors mounted thereon is disposed on the rear side of the solid image pickup device 41 (the back side of the image pickup surface 41a), and the solid image pickup device 41 and the circuit substrate portion 43 are electrically connected.

Figure 2:
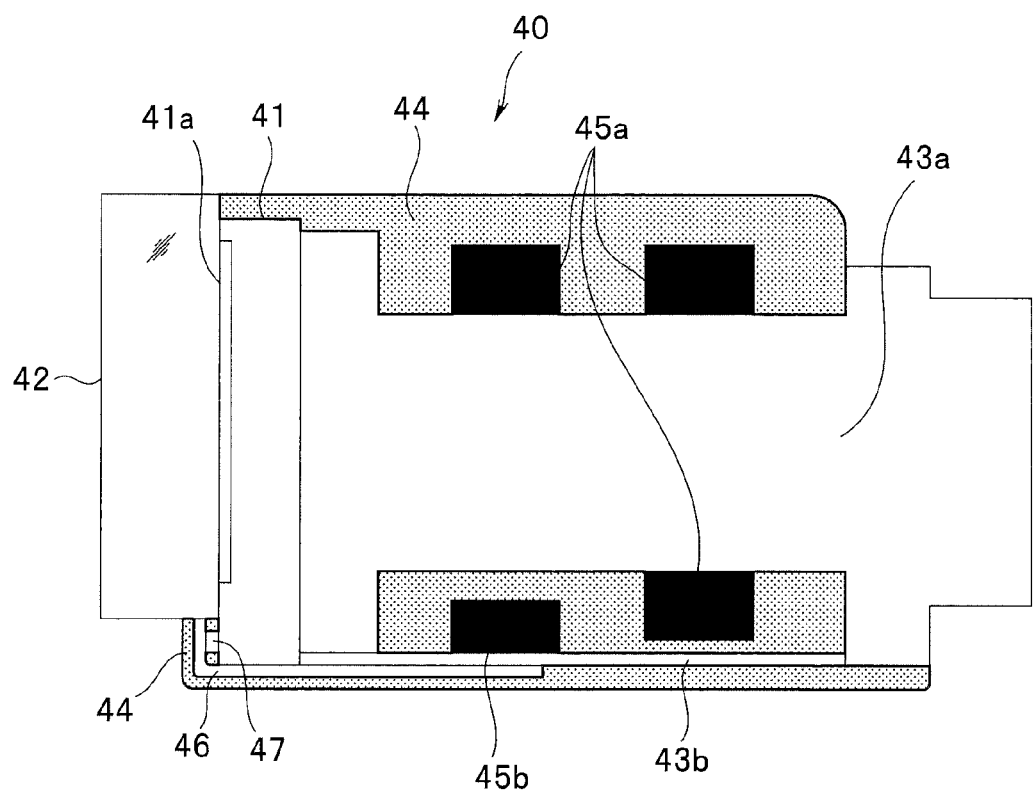
FIG. 2 relates to the first embodiment and is a diagram illustrating a configuration of an image pickup device package.

In the present embodiment, as illustrated in FIG. 2, the image pickup device package 40 includes a multilayer substrate 43a with a plurality of electronic components 45a mounted in a recess portion formed inside, and a flexible substrate 43b with a plurality of electronic components 45b mounted thereon as the circuit substrate portion 43 disposed on the rear side of the solid image pickup device 41. The multilayer substrate 43a and the flexible substrate 43b are electrically connected by means of, for example, bump connection, and furthermore, an inner lead 46 extending from the flexible substrate 43b is connected to a bonding portion 47 provided at a site on the image pickup surface 41a side of the solid image pickup device 41, the site being not covered by the cover glass 42.

Such image pickup device package 40 is formed by integral molding performed in such a manner that the substrates 43a and 43b and the electronic components 45a and 45b are sealed via the sealing resin 44 and the sealing resin 44 covers up to an upper face of the inner lead 46 connected to the bonding portion 47 of the solid image pickup device 41, and an entire side of the cover glass 42 is not covered by the sealing resin. In other words, an upper face portion of the inner lead 46 disposed on a surface of the solid image pickup device 41 that is not covered by the cover glass 42 is sealed by a minimum amount of resin that can protect the relevant electronic equipment part, and thus, even if the sealing resin 44 thermally expands because of temperature change, no undue load is imposed on the cover glass 42 and/or the portion of connection between the inner lead 46 and the bonding portion 47. Accordingly, cracking of the cover glass 42 and/or a failure in connection in the portion of connection between the inner lead 46 and the bonding portion 47 in the image pickup device package 40 due to stress caused by, e.g., transportation before assembly of the image pickup unit 30 can be avoided. Note that on the rear end side of the multilayer substrate 43a, a portion of connection with the signal cable 70 is provided, and the portion of connection is exposed without being covered by the sealing resin 44.

In the image pickup device package 40 formed by integral molding using the sealing resin 44, a cover glass 32 for centering, which is fixed on the inner diameter side of the image pickup frame 31 so as to face the fifth lens 26, is adhered and joined to the cover glass 42 via, e.g., a translucent optical adhesive. In other words, the image pickup device package 40 is held to the image pickup frame 31 via the cover glass 32 for centering. Furthermore, with the signal cable 70 connected to the image pickup device package 40, a shield frame 33 is fitted on an outer circumference on the rear end side of the image pickup frame 31, and the image pickup device package 40 is fixed by an adhesive 60 including, e.g., a thermoset resin charged between the image pickup frame 31 and the image pickup device package 40 and between the shield frame 33, and image pickup device package 40 and the portion of connection with the signal cable 70. Note that a range from an outer circumference of the shield frame 33 to the distal end side of the signal cable 70 is covered by a protection tube 34 including, e.g., a heat-shrinkable tube.

The above-described image pickup device package 40 is one contemplated for use in a front-view endoscope for observation in a direction along a direction of insertion of the endoscope. However, a configuration similar to the above can be employed in a side-view endoscope for observation in a direction substantially perpendicular to the insertion direction.

Figure 3:
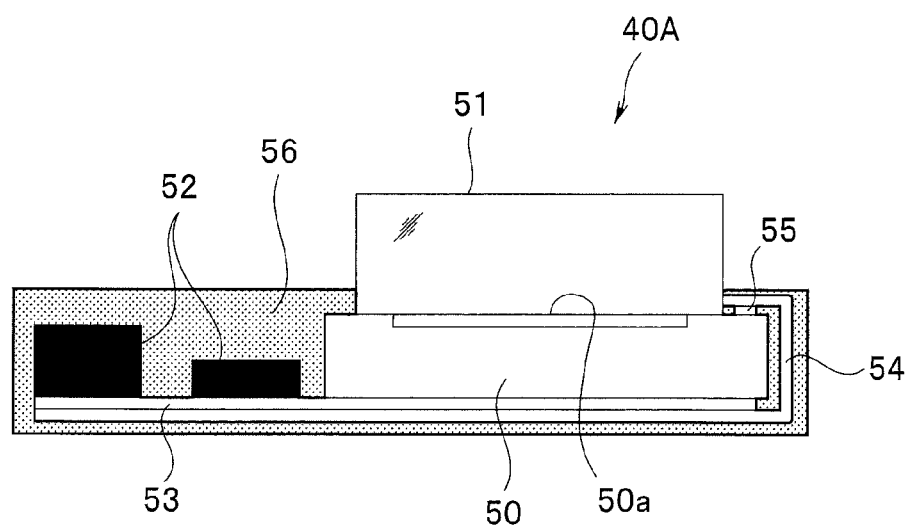
FIG. 3 relates to the first embodiment and is a diagram illustrating a configuration of another image pickup device package.

For example, an image pickup device package 40A, which is illustrated in FIG. 3, is one in which an image pickup surface 50a of a solid image pickup device 50 is directed in a direction perpendicular to an optical axis direction of an objective optical system and, e.g., a non-illustrated prism is disposed on an upper face of a cover glass 51. In the image pickup device package 40A, on the lower side of the solid image pickup device 50 (the back side of the image pickup surface 50a), a flexible substrate 53 with a plurality of electronic components 52 mounted thereon is arranged and an inner lead 54 extending from the flexible substrate 53 is connected to a bonding portion 55 provided on a site of the image pickup surface 50a of the solid image pickup device 50 that is not covered by the cover glass 51. Then, integral molding is performed using an insulating sealing resin 56 so that the electronic components 52 and the flexible substrate 53 are sealed by the sealing resin 56 and the sealing resin 56 covers up to an upper face of the inner lead 54 connected to the bonding portion 55, thereby forming the image pickup device package 40A.

Next, a fixing structure for the signal cable 70 connected to the image pickup device package 40 will be described. Referring back to FIG. 1, the signal cable 70 is fixed together with the image pickup device package 40 via the adhesive 60 with a plurality of electric wires 70b exposed from an outer covering 70a in the vicinity of an end portion of the shield frame 33 fitted on the image pickup frame 31 and with the electric wires 70b connected to the image pickup device package 40 via, for example, soldering.

Here, a part around a strip end of the outer covering 70a from which the electric wires 70b are exposed is fixed by a cable fixing thread 71, and further covered by an elastic tube 72 having a predetermined length. The distal end side of the elastic tube 72 is fixed by another cable fixing thread 73 at a position that is somewhat on the rear side relative to the cable fixing thread 71, and a rear end of the elastic tube 72 is provided so as to extend up to the rear of a bending portion of the endoscope. Furthermore, the distal end side of the elastic tube 72 is covered by a heat-shrinkable tube 74. The part around the strip end of the signal cable 70 doubly covered by the elastic tube 72 and the heat-shrinkable tube 74 is finally fixed by an adhesive 75 charged in addition to the adhesive 60 for fixing the image pickup device package 40 and the electric wires 70b inside the protection tube 34 covering the shield frame 33. Also, a rear end of the heat-shrinkable tube 74 is disposed at a position that is on the rear side relative to a rear end of the protection tube 34, and is on the front side relative to a joint portion between a rigid portion, which is not bent, on the distal end side of the insertion portion of the endoscope and a bending portion, which includes a plurality of bending pieces. In addition, the heat-shrinkable tube 74 includes an elastic material.

In such fixing structure for the signal cable 70, the elastic tube 72 and the heat-shrinkable tube 74, which each hold the signal cable 70 with a gap between the outer covering 70a and the elastic tube 72 or the heat-shrinkable tube 74, exist at the rear of a portion rigidly fixed by the adhesive 60, which results in provision of a part whose hardness gently changes from the rigid part to a flexible part of the cable itself. Accordingly, even if an outer force in a bending direction is acted on the signal cable 70, the signal cable 70 is gently curved without partial concentration of stress, enabling prevention of disconnection of the inner electric wires.

Next, a second embodiment of the present invention will be described with reference to FIG. 4.

Figure 4:
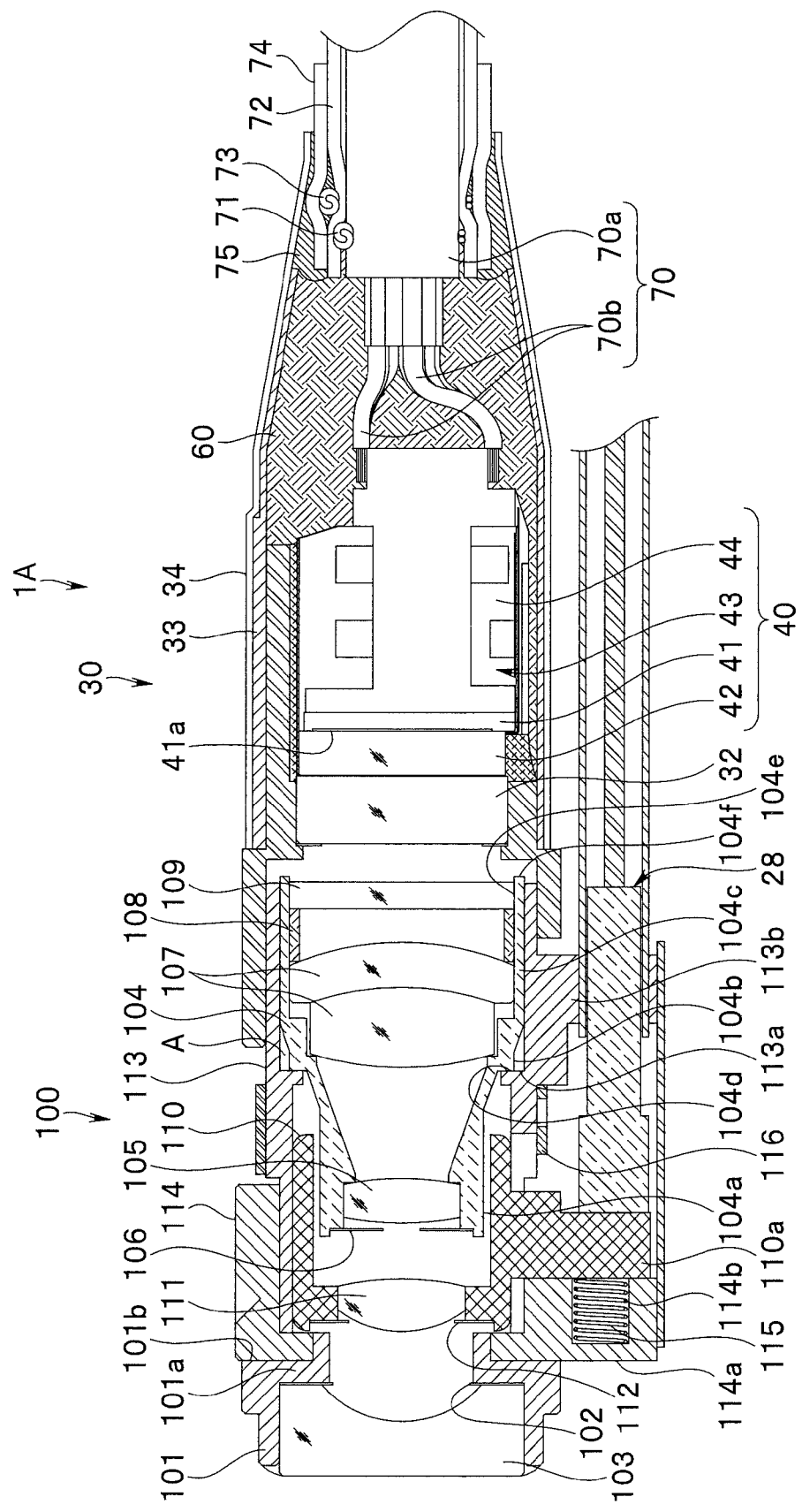
FIG. 4 relates to a second embodiment of the present invention and is a configuration diagram illustrating an image pickup apparatus provided at a distal end of an insertion portion of an endoscope.
Figure 5:
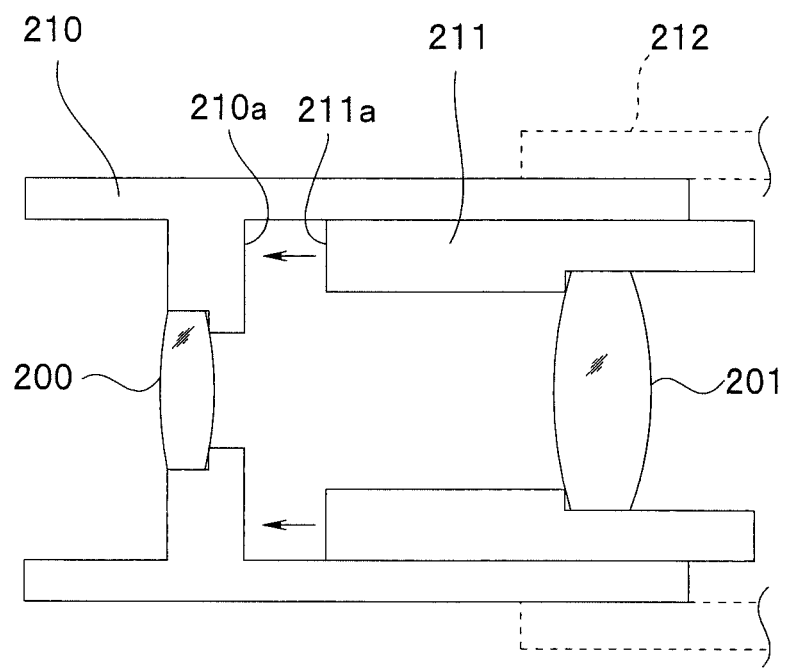
FIG. 5 is a diagram illustrating a conventional lens holding structure.

In FIG. 4, an image pickup apparatus 1A includes an objective optical system unit 100, and an image pickup system unit 30 that is arranged at the rear of the objective optical system unit 100 and is similar to that of the first embodiment.

The above-described objective optical system unit 100 is joined to the image pickup system unit 30, and an incoming light entering via an objective lens group forms an image on a light-receiving surface of a solid image pickup device 41 inside the image pickup system unit 30. Then, the optical image of a subject/object is subjected to photoelectric conversion by the solid image pickup device 41, and an image pickup signal resulting from the photoelectric conversion is transmitted to a following signal processing circuit via a signal cable.

The objective optical system unit 100 includes a first lens frame 101 holding a first lens group, a moving lens frame 110 holding a moving lens group, a second lens frame 104 holding remaining lens groups, a third lens frame 113 receiving the moving lens frame 110 and holding the second lens frame 104, a fourth lens frame 114 holding the first lens frame 101 and the third lens frame 113, and an adjustment ring 116 that fits on an outer shape of the third lens frame 113.

The third lens frame 113 receives the moving lens frame 110, and holds a second lens frame 104. The third lens frame 113 is formed so as to have a substantially-cylindrical shape, and an inner surface of the cylindrical shape portion serves as a slide surface on which the moving lens frame 110 advances and retracts. Furthermore, in the cylindrical shape portion, a slit for disposition of an action portion 110a of the moving lens frame 110 that is advanced and retracted by an actuator 28. Furthermore, respective lenses in the first lens group, the second lens group and the moving lens group are disposed at sites in the respective lens frames where perpendicularity and coaxiality are provided by means of high-precision processing. With such structure, the respective lenses in the first lens group, the second lens group and the moving lens group are disposed in the respective lens frames without inclination.

Also, on the inner surface of the cylindrical shape, a step portion 113a is provided. On the rear side of the step portion 113a, a space portion that receives the second lens frame 104 is provided. Also, on an outer surface of the cylindrical shape portion, a projection portion 113b for disposing an actuator 28 is provided.

The fourth lens frame 114 is formed so as to have a substantially-cylindrical shape, and holds the first lens frame 101 and the third lens frame 113. On an outer surface of the cylindrical shape, a projection portion 114a is provided. In the projection portion 114a, a recess portion 114b that receives a spring 115 brought into contact with the action portion 110a of the moving lens frame 110 is provided.

Note that if the first lens frame 101 is employed in, for example, an endoscope, the first lens frame 101 is fitted in a distal end frame of the endoscope, which is not illustrated, and held by a distal end portion of the endoscope.

The first lens frame 101 is formed in a substantially-cylindrical shape, and at a position close to a distal end in an inner portion of the cylindrical shape, a flange portion 101a, which an outer circumferential portion on the proximal end side of the first lens 103 is brought into contact with via a first diaphragm 102 is provided. On the rear side of the flange portion 101a, a contact portion 101b brought into contact with the fourth lens frame 114 and a projection portion that fits in the fourth lens frame 114 are provided.

Note that if the first lens frame 101 is employed in, for example, an endoscope, the first lens frame 101 is brought into contact with a distal end frame of the endoscope, which is not illustrated, in an optical axis direction, whereby positioning of the image pickup apparatus relative to the distal end frame of the endoscope is determined.

The second lens frame 104 holds the remaining lens groups of the objective lens group other than the first lens group and the moving lens group, and holds a third diaphragm 106, a third lens 105, a cemented lens 107, a spacer 108 and a first filter 109 disposed at the rear of the moving lens group in this order from the distal end side. The second lens frame 104 holding these lens groups is inserted into the space portion provided on the rear side of the step portion of the third lens frame 113, an intermediate portion of the second lens frame 104 is brought into contact with an end face on the rear side of the step portion of the second lens frame 104, and a rear end portion of the second lens frame 104 is fitted on an inner wall surface of the space portion of the third lens frame 113 and fixed via, e.g., an adhesive.

The second lens frame 104 is formed in a stepped substantially-cylindrical shape in which a distal end projection portion 104a, the intermediate portion 104b and a rear end portion 104c have different outer diameters in the outer shape, and the second lens frame 104 includes a contact portion 104d via which the intermediate portion 104b having a cylindrical shape with a diameter smaller than an inner diameter of the space portion of the third lens frame 113 is brought into contact with the end face on the rear side of the step portion of the third lens frame 113, and a cylindrically-shaped fitting portion 104e provided over a predetermined length on the rear end side of the contact portion 104d, the fitting portion 104e having a diameter larger than that of the contact portion 104d and being fitted on the inner wall surface of the space portion of the third lens frame 113. In other words, the second lens frame 104 is formed in a shape that forms a gap A between the inner wall surface of the space portion of the third lens frame 113 and the second lens frame 104 when the second lens frame 104 is inserted into the space portion of the third lens frame 113. Furthermore, a surface of a distal end portion of the second lens frame 104 and the end face on the rear side of the step portion of the third lens frame 113 are processed so as to have highly-precise perpendicularity to the optical axis. Furthermore, the fitting portion 104e is processed so as to have highly-precise coaxiality relative to the optical axis.

As a result of provision of such gap, when the second lens frame 104 is inserted and fitted in the third lens frame 113, the area of contact between the third lens frame 113 and the second lens frame 104 is reduced and the insertion resistance is thereby reduced, enabling enhancement in assembling workability. In addition, the intermediate portion 104b of the second lens frame 104 can reliably be brought into contact with an end face of the step portion 113a of the third lens frame 113, whereby variations in position in the optical axis direction are eliminated, enabling provision of a stable optical precision, and thus, variations in coaxiality and/or perpendicularity and/or position in optical axis direction between the first lens 103 disposed in the first lens frame 101 and the remaining lens groups disposed inside the second lens frame 104 are eliminated, enabling prevention of optical performance deterioration.

Also, in order to provide optical precision, it is only necessary that only the rear end portion is fitted, and thus, the length of the fitting portion that requires a precise dimensional tolerance can be reduced, and if there is difficulty in processing the frame, employment of the present structure provides a cost reduction effect. Furthermore, when an adhesive is applied to the fitting portion 104e of the second lens frame 104 and the fitting portion 104e is assembled into the third lens frame 113, even if the adhesive applied on the fitting portion 104e flows toward the distal end side, the adhesive can be confined inside the gap A, and does not flow between the end face of the step portion 113a of the third lens frame 113 and the distal end of the contact portion 104d of the second lens frame 104. Accordingly, no misalignment in the optical axis direction among the lenses by the amount of a thickness of the layer of the flowed-in adhesive resulting from the adhesive flowing to the contact surface occurs, ensuring provision of a stable optical precision.

Furthermore, a length from the contact portion 104d of the second lens frame 104 to the rear end of the third lens frame 113 is made to be longer than a length from the step portion 113a of the third lens frame 113 to a rear end of the third lens frame 113, thereby providing an assembling portion 104f.

As a result of provision of such assembling portion 104f and the gap A, the assembling portion 104f is pushed when the second lens frame 104 is fitted in the third lens frame 113 and thus, no undue load is imposed on the first filter 109 and/or the cemented lens 107 via the first filter 109 and the spacer 108, ensuring that worst situations such as breakage of the first filter 109 and/or the cemented lens 107 are avoided.

Furthermore, the second lens frame 104 includes a distal end projection portion 104a holding the third lens 105 disposed so as to project in the moving lens frame 110 on the front side relative to the step portion of the third lens frame 113 and having a diameter smaller than an inner diameter of moving lens frame 110.

Provision of such distal end projection portion 104a enables the slide surface of the third lens frame 113 to have a long length in the optical axis direction, and since a slide stroke from a WIDE position to a TELE position of the moving lens frame 110 is set according to an optical design, enabling the slide surface of the moving lens frame 110 to have a long length in the optical axis direction. Consequently, when the moving lens frame 110 is advanced and retracted by an operation of the actuator 28, inclination of the moving lens frame 110 relative to the diameter direction of the third lens frame 113 can be suppressed, enabling provision of stable optical performance and smooth advancing and retracting operation of the moving lens frame 110.

The moving lens frame 110 holds a second diaphragm 112 and a moving lens 111. The moving lens frame 110 is formed in a cylindrical shape, and an outer surface of the cylindrical shape portion serves as a slide surface that slides on the third lens frame 113, and furthermore, on the outer surface of the cylindrical shape portion, a projection-shaped action portion 110a on which a force from the actuator 28 acts is provided.

Next, a fixing structure for a signal cable 70 connected to the image pickup device package 40 will be described. As in the first embodiment illustrated in FIG. 1, the signal cable 70 is fixed together with an image pickup device package 40 via an adhesive 60 with a plurality of electric wires 70b exposed from an outer covering 70a in the vicinity of an end portion of a shield frame 33 fitted on an image pickup frame 31 and with the electric wires 70b connected to the image pickup device package 40 via, for example, soldering.

Here, a part around a strip end of the outer covering 70a from which the electric wires 70b are exposed is fixed by a cable fixing thread 71, and further covered by an elastic tube 72 having a predetermined length. The distal end side of the elastic tube 72 is fixed by another cable fixing thread 73 at a position that is somewhat on the rear side relative to the cable fixing thread 71, and a rear end of the elastic tube 72 is provided so as to extend up to the rear of a bending portion of the endoscope. Furthermore, the distal end side of the elastic tube 72 is covered by a heat-shrinkable tube 74. The part around the strip end of the signal cable 70 doubly covered by the elastic tube 72 and the heat-shrinkable tube 74 is finally fixed by an adhesive 75 charged in addition to the adhesive 60 for fixing the image pickup device package 40 and the electric wires 70b inside the protection tube 34 covering the shield frame 33. Also, a rear end of the heat-shrinkable tube 74 is disposed at a position that is on the rear side relative to a rear end of the protection tube 34 and is on the front side relative to a joint portion between a rigid portion, which is not bent, on the distal end side of an insertion portion of the endoscope and a bending portion, which includes a plurality of bending pieces. In addition, the heat-shrinkable tube 74 includes an elastic material.

In such fixing structure for the signal cable 70, the elastic tube 72 and the heat-shrinkable tube 74, which each hold the signal cable 70 with a gap between the outer covering 70a and the elastic tube 72 or the heat-shrinkable tube 74, exist at the rear of a portion rigidly fixed by the adhesive 60, which results in provision of a part whose hardness gently changes from the rigid part to a flexible part of the cable itself. Accordingly, even if an outer force in a bending direction is acted on the signal cable 70, the signal cable 70 is gently curved without partial concentration of stress, enabling prevention of disconnection of the inner electric wires.

As in the above-described first embodiment, the objective optical system unit 100 and the image pickup system unit 30 are joined to each other by inserting and fitting the third lens frame 113 with the second lens frame 104 received and fixed thereto into an inner diameter portion of the image pickup frame 31 holding the image pickup device package 40 and joining these two members to each other in an air-tight manner. The image pickup device package 40 is one resulting from unitization by means of integral molding as in the above-described first embodiment.

The image pickup device package 40 in the present embodiment also employs a configuration similar to that illustrated in FIG. 2 as in the above-described first embodiment.

What is claimed is:

1. An image pickup apparatus including an image pickup system disposed at a rear of an objective optical system,
    wherein the objective optical system includes a plurality of lenses and a plurality of lens frames, and in at least two lens frames of the plurality of lens frames,
    a first lens frame includes a step portion inside, which a distal end portion of a second lens frame is brought into contact with,
    the second lens frame includes a contact portion having a distal end portion to be brought into contact with the step portion with a gap provided between the inner diameter of the first lens frame, and a fitting portion which is provided on a rear side relative to the contact portion in an optical axis direction, has a diameter larger than a diameter of the contact portion, and fits on an inner wall surface of the first lens frame.

2. The image pickup apparatus according to claim 1, wherein a rear end of the second lens frame projects toward a rear side relative to a rear end of the first lens frame, and the rear end of the first lens frame and the rear end of the second lens frame are open ends.

* * * * *